United States Patent [19]

Tuba et al.

[11] Patent Number: 5,591,735
[45] Date of Patent: Jan. 7, 1997

[54] ANDROSTANE DERIVATIVES SUBSTITUTED BY A QUATERNARY AMMONIUM GROUP IN 16-POSITION, PHARMACEUTICAL COMPOSITIONS CONTAINING THEM AND PROCESS FOR PREPARING SAME

[75] Inventors: Zoltan Tuba; E. Szilveszter Vizi, both of Budapest, Hungary; Francis F. Foldes, Key Biscayne, Fla.; Sandor Maho, Budapest, Hungary

[73] Assignee: Marvishi Pharmaceutical Co., Ltd., Osaka, Japan

[21] Appl. No.: 141,535

[22] Filed: Oct. 27, 1993

[30] Foreign Application Priority Data

Nov. 2, 1992 [HU] Hungary ................ P9203436

[51] Int. Cl.⁶ .............. C07J 43/00; A61K 31/58
[52] U.S. Cl. ................ 514/172; 540/96; 540/97
[58] Field of Search ............. 540/97, 96; 514/172

[56] References Cited

U.S. PATENT DOCUMENTS 4,177,190  12/1979  Tuba et al. ............ 260/239.5

FOREIGN PATENT DOCUMENTS 0287150  10/1988  European Pat. Off. .
2194434   3/1974  France .
 247448   4/1993  New Zealand .

OTHER PUBLICATIONS

Buckett et al, Jour. of Med. Chemistry vol. 16 pp. 1116–1124 (1973).

Zoltan Tuba et al., "Structure–Activity Relationships of Steroidal Neuromuscular Blocking Agents", Molecular Structure and Bioilogical Activity of Steroids, Chapter 11, pp. 359–397 (Aug. 1992).

*Primary Examiner*—Mukund J Shah
*Assistant Examiner*—Anthony Bottino
*Attorney, Agent, or Firm*—Foley & Lardner

[57] ABSTRACT

There is disclosed novel, therapeutically active androstane derivatives having neuromuscular blocking effect, which are substituted by a quaternary ammonium group in 16-position; pharmaceutically composition containing them; process for producing them; and novel intermediates for the production.

8 Claims, No Drawings

ANDROSTANE DERIVATIVES SUBSTITUTED BY A QUATERNARY AMMONIUM GROUP IN 16-POSITION, PHARMACEUTICAL COMPOSITIONS CONTAINING THEM AND PROCESS FOR PREPARING SAME

FIELD OF THE INVENTION

The invention relates to novel, therapeutically active androstane derivatives having neuromuscular blocking effect, which are substituted by a quaternary ammonium group in 16-position; pharmaceutical compositions containing them; process for producing them; and novel intermediates for the production.

BACKGROUND OF THE INVENTION

The large number of literature references, patent applications as well as scientific publications proves the therapeutic importance of neuromuscular blocking agents.

The first important results of the research on steroidal neuromuscular blocking agents are described in the United Kingdom patent specification No. 1,138,605 or the equivalent Hungarian patent specification No. 154,368, respectively. In these patents, the synthesis of 2β,16β-bis-(amino)-3α,17β-diacetoxy-5α-androstane derivatives and their quaternary salts are described. These compounds contain piperidino, morpholino or alkylamino groups in the 2- and 16-positions of the steroid skeletons. Thus, quaternary centers can be formed only on the nitrogens bound to the C-2 and C-16 carbon atom.

The synthesis described in the above-cited patent specifications and the biological results obtained are summarized in: J. Medicinal Chemistry 16, 1116 (1973).

From these compounds, pancuronium bromide (chemically,1'-[3α,17β-bis(acetyloxy)-5α-androstane-2β,16β-diyl]bis[1-methylpiperidinium]dibromide) became a therapeutically employed neuromuscular blocking agent with long duration and non-depolarizing mechanism of action.

Due to its shorter duration of action and lack of cardiovascular side effects, vecuronium bromide (chemically 1-[3α,17β-bis(acetyloxy)-2β-(1-piperidinyl)androstan-16β-yl]1-methylpiperidinium bromide hydrochloride), a derivative which is structurally close to pancuronium bromide, except that it contains a single quaternary group on the nitrogen connected to C-16 carbon atom, is more advantageous than pancuronium and other bisquaternary derivatives. The preparation of vecuronium is described in the Hungarian patent specification No. 181,847 which is equivalent to the European patent specification No. 0,008,824.

A more recent important result in the research of neuromuscular blocking drugs is published in the Hungarian patent specification No. 165,600. From the compounds published therein, the effectivity as well as the cardiovascular stability of pipecuronium bromide (chemically 4,4'-[3α,17β-bis(acetyloxy)-5α-androstane-2β,16β-diyl]bis[1,1-dimethylpiperazinium]dibromide) exceed those of pancuronium bromide or vecuronium bromide.

The synthesis of quaternary derivatives of bis(amino)androstanes are furthermore described in the European patent specification Nos. 0,208,497, 0,330,253 and 0,288,102 as well as in the Hungarian patent specification Nos. 172,522 and 172,521. The compounds published in these latter patent applications cited have not been utilized in therapy.

The synthesis of quaternary derivatives of the so-called aza-aminosteroids having a different chemical structure is described in the Hungarian patent specification No. 175,287. In spite of their rapid onset and short duration of action, because of their unwanted cardiovascular effects, these latter compounds have not been used therapeutically.

In spite of the fact that pancuronium bromide, vecuronium bromide as well as pipecuronium bromide are widely used in clinical practice, there is a constant demand in medicine for compounds possessing more desirable properties (e.g. more rapid onset of action).

A neuromuscular blocking agent, favorable for clinical use, should have a non-depolarizing mechanism of action, should not have vagolytic or ganglion-blocking effects or cause histamine release and should possess good cardiovascular stability. Another demand is a rapid onset of action allowing earlier intubation. This, from the viewpoint of anesthetical practice, is an important safety factor. A further demand is for short duration of action, which contributes to controllability and safety of these compounds during surgical interventions.

OBJECTS OF THE INVENTION

The main object of the present invention is to provide compounds which are qualitatively superior, in comparison to the prior art, having cardiovascular stability as well as rapid onset and short duration of action.

Another object of the present invention is to provide a process for producing the above compounds.

Further, the object of the present invention is to provide novel intermediates for the above process.

These objects as well as other objects and advantages of the present invention will become apparent to those skilled in the art from the following description.

SUMMARY OF THE INVENTION

Surprisingly, it has been found that androstane compounds of formula (I) substituted by a quaternary amino group in 16-position have a rapid onset and short duration of action, and show good cardiovascular stability. Thus, the present invention has been completed.

According to the present invention, there is provided an androstane derivative of the formula (I)

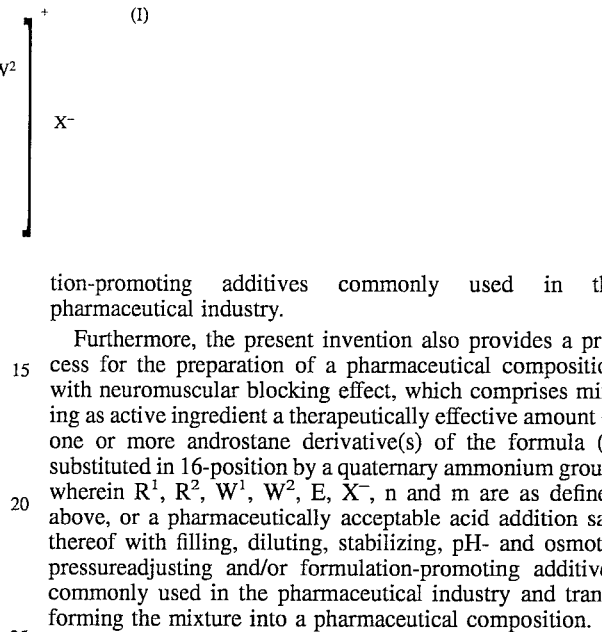

substituted in 16-position by a quaternary ammonium group, wherein $R^1$ means hydrogen or a $C_{1-4}$ alkanoyl group;

$R^2$ stands for hydrogen or a $C_{1-4}$ alkanoyl group;

$W^1$ and $W^2$ represent the same or different $>CR^3R^4$ group each; or the one of them means a chemical bond (valence) and the other is $>CR^3R^4$ group; or $W^1$ means a $>CR^3R^4$ group and $W^2$ is an $>NER^5$ group; one of $R^3$ and $R^4$ is hydrogen and the other is an —$OR^1$ group, wherein $R^1$ is as defined above; or $R^3$ and $R^4$ together stand for an oxo group or a $C_{2-5}$ alkylenedioxy group;

$R^5$ stands for $C_{1-4}$ alkyl or $C_{3-5}$ alkenyl group;

E means a $C_{1-4}$ alkyl or $C_{3-5}$ alkenyl group with the proviso that, in derivatives containing a ring with two nitrogen atoms, the substituent E has the above meaning only in the case when it is bound to the nitrogen indirectly connected to the steroid skeleton, whereas the other one means alone electron pair;

$X^-$ is the equivalent amount of an anion; and n and m, independently from another, are 1, 2, 3 or 4, with the proviso that the sum of n and m is 4, 5, 6 or 7 within one ring, independently from their value in the other ring, as well as their acid addition salts. $R^2$ in the above formula is preferably $C_{1-4}$ alkanoyl group.

DETAILED DESCRIPTION OF THE INVENTION

The main structural difference of these compounds from substances, described up to the present, lies therein that at least one of the amine substituents bears a hydroxyl, $C_{1-4}$ alkanoyloxy, oxo or $C_{2-5}$ alkylenedioxy group. In comparison to the known active compounds (drugs), these properties result in a more favorable possibility of therapeutical utilization.

The compounds of formula (I) have neuromuscular blocking effect. Accordingly, the invention also provides a method of treatment, which comprises of the administration of one or more therapeutically effective dose(s) of a compound of formula (I), or pharmaceutically acceptable acid addition salt thereof, alone or in the form of pharmaceutical composition, into the organism of mammal (including man) for blocking the transmission of nerve impulses to striated muscles.

Further, the present invention also provides a pharmcaeutical composition with neuromuscular blocking effect, which comprises as active ingredient a therapeutically effective amount of one or more androstane derivative(s) of the formula (I) substituted in 16-position by a quaternary ammonium group, wherein $R^1$, $R^2$, $W^1$, $W^2$, E, $X^-$, n and m are as defined above, or a pharmaceutically acceptable acid addition salt thereof, in admixture with filling, diluting, stabilizing, pH- and osmotic pressure-adjusting and/or formulation-promoting additives commonly used in the pharmaceutical industry.

Furthermore, the present invention also provides a process for the preparation of a pharmaceutical composition with neuromuscular blocking effect, which comprises mixing as active ingredient a therapeutically effective amount of one or more androstane derivative(s) of the formula (I) substituted in 16-position by a quaternary ammonium group, wherein $R^1$, $R^2$, $W^1$, $W^2$, E, $X^-$, n and m are as defined above, or a pharmaceutically acceptable acid addition salt thereof with filling, diluting, stabilizing, pH- and osmotic pressureadjusting and/or formulation-promoting additives commonly used in the pharmaceutical industry and transforming the mixture into a pharmaceutical composition.

Further, the present invention also provides a process for producing a compound of the above formula (I), and novel intermediates for the production.

Preferred examles of the compound of the formula (I) include

1-[17β-acetyloxy-2β-(1,4-dioxa-8-azaspiro[4.5]dec-8-yl)-3α-hydroxy-5α-androstan-16β-yl]-1-(2-propenyl)pyrrolidinium bromide;

1-[3α,17β-bis(acetyloxy)-2β-(1,4-dioxa-8-azaspiro[4.5]dec-8-yl)-5α-androstan-16β-yl]-1-methylpyrrolidinium bromide;

1-[3α,17β-bis(acetyloxy)-2β-(1,4-dioxa-8-azaspiro[4.5]dec-8-yl)-5α-androstan-16β-yl]-1-(2-propenyl)pyrrolidinium bromide;

1-[17β-acetyloxy-3α-hydroxy-2β-(4-hydroxy-1-piperidinyl)-5α-androstan-16β-yl]-1-methylpyrrolidinium bromide;

1-[17β-acetyloxy-3α-hydroxy-2β-(4-hydroxy-1-piperidinyl)-5α-androstan-16β-yl]-1-(2-propenyl)pyrrolidinium bromide;

1-[3α,17β-bis(acetyloxy)-2β-(4-hydroxy-1-piperidinyl)-5α-androstan-16β-yl]-1-(2-propenyl)pyrrolidinium bromide;

1-[3α,17β-bis(acetyloxy)-2β-(4-acetyloxy-1-piperidinyl)-5α-androstan-16β-yl]-1-methylpyrrolidinium bromide;

1-[17β-(acetyloxy)-3α-hydroxy-2β-(4-hydroxy-1-piperidinyl)-5α-androstan-16β-yl]-1-methylpiperidinium bromide;

1-[3α,17β-bis(acetyloxy)-2β-(4-hydroxy-1-piperidinyl)-5α-androstan-16β-yl]-1-methylpiperidinium bromide;

4-[3α,17β-bis(acetyloxy)-2β-(1,4-dioxa-8-azaspiro[4.5]dec-8-yl)-5α-androstan-16β-yl]-1,1-dimethylpiperazinium bromide;

4-[3α,17β-bis(acetyloxy)-2β-(1,4-dioxa-8-azaspiro[4.5]dec-8-yl)-5α-androstan-16β-yl]-1-methyl-1-(2-propenyl)-piperazinium bromide;

4-[17β-acetyloxy-3α-hydroxy-2β-(4-hydroxy-1-piperidinyl)-5α-androstan-16β-yl]-1,1-dimethylpiperazinium bromide;

4-[17β-acetyloxy-3α-hydroxy-2β-(4-hydroxy-1-piperidinyl)-5α-androstan-16β-yl]-1-methyl-1-(2-propenyl)piperazinium bromide;

4-[3α,17β-bis(acetyloxy)-2β-(4-oxo-1-piperidinyl)-5α-androstan-16β-yl]-1,1-dimethylpiperazinium bromide;

4-[3α,17β-bis(acetyloxy)-2β-(4-oxo-1-piperidinyl)-5α-androstan-16β-yl]-1-methyl-1-(2-propenyl)piperazinium bromide;

4-[3α,17β-bis(acetyloxy)-2β-(4-hydroxy-1-piperidinyl)-5α-androstan-16β-yl]-1,1-dimethylpiperazinium bromide;

4-[3α,17β-bis(acetyloxy)-2β-(4-hydroxy-1-piperidinyl)-5α-androstan-16β-yl]-1-methyl-(2-propenyl)piperazinium bromide;

4-[3α,17β-bis(acetyloxy)-2β-(4-acetyloxy-1-piperidinyl)-5α-androstan-16β-yl]-1,1-dimethylpiperazinium bromide;

4-[3α,17β-bis(acetyloxy)-2β-(4-acetyloxy-1-piperidinyl)-5α-androstan-16β-yl]-1-methyl-1-(2-propenyl)piperazinium bromide;

8-[3α,17β-bis(acetyloxy)-2β-(1-piperidinyl)-5α-androstan-16β-yl]-8-methyl-1,4-dioxa-8-azoniaspiro[4.5]decane bromide;

8-[3α,17β-bis(acetyloxy)-2β-(4-acetyloxy-1-piperidinyl)-5α-androstan-16β-yl]-8-methyl-1,4-dioxa-8-azoniaspiro[4.5]decane bromide;

4-acetyloxy-1-[3α,17β-bis(acetyloxy)-2β-(4-acetyloxy-1-piperidinyl)-5α-androstan-16β-yl]-1-methylpiperidinium bromide;

1-[3α-acetyloxy-2β-(1,4-dioxa-8-azaspiro[4.5]dec-8-yl)-17β-hydroxy-5α-androstan-16β-yl]-1-(2-propenyl)pyrrolidinium bromide; and 1-[3α,17β-dihydroxy-2β-(1,4-dioxa-8-azaspiro[4.5]dec-8-yl)-5α-androstan-16β-yl]-1-(2-propenyl)pyrrolidinium bromide.

Among them, 1-[3α,17β-bis(acetyloxy)-2β-(1,4-dioxa-8-azaspiro[4.5]dec-8-yl)-5α-androstan-16β-yl]-1-(2-propenyl)pyrrolidinium bromide is particularly preferred.

According to the invention, the compounds of formula (I) as well as their acid addition salts are prepared in such a way that:

a) in order to obtain androstane derivatives of formula (I) containing a $>CR^3R^4$ group as $W^1$ and a valence bond or $>NER^5$ group as $W^2$, where $R^1$, $R^2$, $R^3$, $R^4$, $R^5$, E, $X^-$, n and m are as defined for formula (I), a 17β-hydroxy-16-amino-2α,3α-epoxyandrostane derivative of formula (IVa):

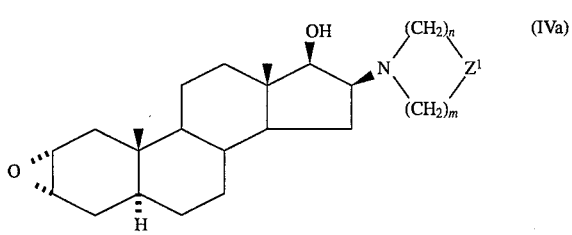

wherein m and n are as defined above and $Z^1$ means a valence bond or an $>NR^5$ group, wherein $R^5$ is as defined above, is reacted with a heterocyclic amine of formula (VII):

wherein m and n are as defined above, and Z means a $>CR^3R^4$ group, wherein $R^3$ and $R^4$ are as defined above; thereafter, if desired, the obtained 3α,17β-dihydroxy-2α,16β-diaminoandrostane derivatives of formula (IIIa):

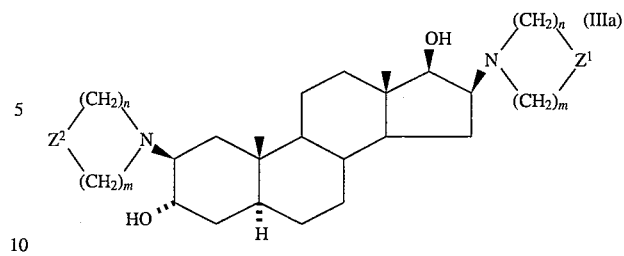

wherein n, m and $Z^1$ are as defined above, and $Z^2$ is the same as Z defined above, i) is treated with an acid for hydrolyzing the $C_{2-5}$ alkylenedioxy group standing for $R^3$ and $R^4$ to form an oxo group; and/or ii) is reduced to transform the oxo group, standing for $R^3$ and $R^4$ to a hydroxyl group; and is acetylated on its 17-hydroxyl group or, if desired, on one more of its other hydroxyl group(s) with a reactive derivative of a $C_{1-4}$ alkanecarboxylic acid in one or more acylating phase(s) before hydrolyzing the alkylenedioxy group, and/or before and/or after reducing the oxo group; finally, the acylated 3α,17β-dihydroxy-2β,16β-diaminoandrostane derivative of formula (IIa) obtained:

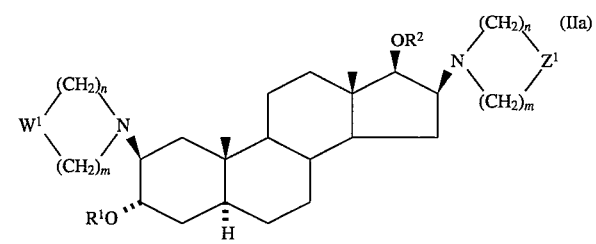

wherein $W^1$ is as defined for the present process, $Z^1$, n, m, $R^1$ and $R^2$ are as defined above, is quaternized with a $C_{1-4}$ alkyl or $C_{3-5}$ alkenyl halide; or b) in order to obtain androstane derivatives of formula (I) containing a valence bond or $>CR^3R^4$ group as $W^1$ and $>CR^3R^4$ group as $W^2$, where $R^1$, $R^2$, $R^3$, $R^4$, E, $X^-$, n and m are as defined for formula (I), a 17β-halo-2α,3α:16α,17α-diepoxyandrostane derivative of formula (VI):

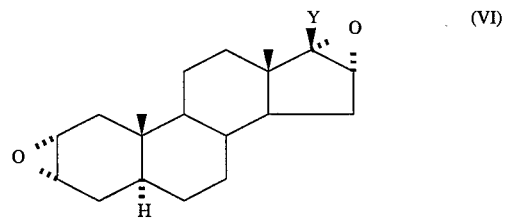

wherein Y is halogen, is reacted with a heterocyclic amine derivative of formula (VII), wherein n and m are as defined above and Z represents a $>CR^3R^4$ group, where $R^3$ and $R^4$ are as defined above;

the obtained 17-oxo-16β-amino-2α,3α-epoxyandrostane derivative of formula (V):

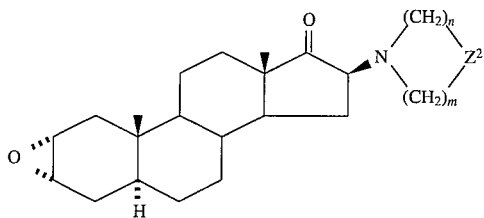

wherein n and m are as defined above, and $Z^2$ which is the same as Z defined above, is reduced by an alkaline metal borohydride;

the obtained 17β-hydroxy-16β-amino-2α,3α-epoxyandrostane derivative of formula (IVb):

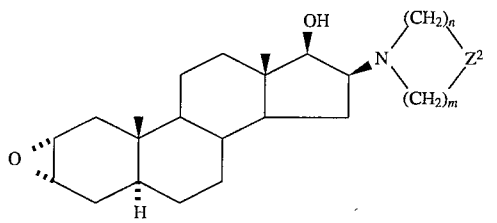

wherein m, n and $Z^2$, as defined above is reacted with a heterocyclic amine derivative of formula (VII), wherein n and m are as defined above, and Z represents a valence bond or >$CR^3R^4$ group, wherein $R^3$ and $R^4$ are as defined above; if desired, the obtained 3α,17β-dihydroxy-2β,16β-diaminoandrostane derivative of formula (IIIb):

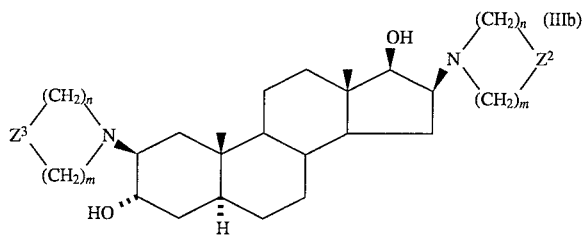

wherein n, m and $Z^2$ are as defined above, and $Z^3$ is the same as Z defined in the latter case, i) can be treated with an acid for hydrolyzing the $C_{2-5}$ alkylenedioxy group standing for $R^3$ and $R^4$ to form an oxo group; and/or ii) is reduced to transform the oxo group standing for $R^3$ and $R^4$ to a hydroxyl group; and is acetylated on its 17-hydroxyl group or, if desired, on one or more of its other hydroxyl group(s) with a reactive derivative of a $C_{1-4}$ alkanecarboxylic acid in one or more acylating phase(s) before hydrolyzing the alkylenedioxy group and/or before and/or after reducing the oxo group;

finally, the acetylated 3α,17β-dihydroxy-2β,16β-diaminoandrostane derivative of formula (IIb) obtained:

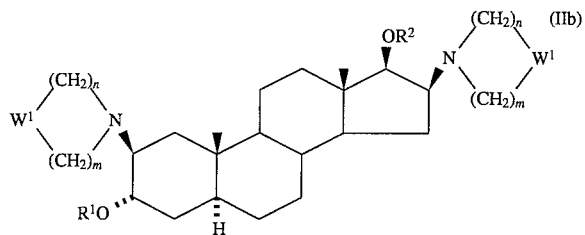

wherein $W^1$ and $W^2$ are as defined for the present process, and n, m, $R^1$ and $R^2$ are as defined for formula (I), is quaternized with a $C_{1-4}$ alkyl or $C_{3-5}$ alkenyl halide;

then, if desired, the obtained androstane derivative of formula (I) substituted by a quaternary ammonium group in 16-position wherein $R^1$, $R^2$, $W^1$, $W^2$, $R^3$, $R^4$, $R^5$, E, $X^-$, n and m are as defined above, is converted to an acid addition salt by treating it with a nontoxic mineral or organic acid.

Compounds of formulae (IIb) and (IIIb) are symmetric or asymmetric diamines depending thereon that the amine moieties connected to the 2β- and 16β-positions of the steroid skeleton are the same or different.

In addition to the compounds of formula (I), according to the invention, several intermediates of the process such as those described in formulae (IIa), (IIb), (IIIa) and (IIIb) are novel. The intermediates of formulae (V) and (IVb) containing >$CR^3R^4$ group as $Z^2$, wherein one of $R^3$ and $R^4$ is hydrogen, and the other is a hydroxyl group, or $R^3$ and $R^4$ together stand for a $C_{2-4}$ alkylenedioxy group, are also novel. The present invention also provides these novel compounds.

17β-Hydroxy-16-amino-2α,3α-epoxyandrostane derivatives of formula (IVa) and 17β-halo-2α,3α:16α,17α-diepoxyandrostane derivatives of formula (VI) used as starting substances in the process according to the invention are described in the Hungarian patent specifications Nos. 172, 522 and 171,166, respectively.

According to process a), the compounds of formula (IVa) are preferably reacted with 1,4-dioxa-8-azaspiro[4.5]decane or 4-hydroxypiperidine in the presence of water or in a mixture of an inert organic solvent, e.g. n-propanol and water, at the boiling point of the reaction mixture. The progress of the reaction is observed by thin layer chromatography (TLC). After completion of the reaction (which requires 70 to 100 hours), the excess of the amine used, as well as the solvent, are distilled off and after precipitating the residue with water and filtration, the precipitate is washed with water until free of mother liquor and then dried. Alternatively, the precipitate may be mixed e.g. with acetonitrile or acetone and after compacting, the precipitate is filtered, washed until free of mother liquor, dried and when necessary recrystallized.

One or more hydroxyl group(s) of the obtained 3α,17β-dihydroxy-2α,16β-diaminoandrostane derivatives of formula (IIIa) is (are) preferably esterified in the following way: After dissolving the compounds of formula (IIIa) in a halogenated hydrocarbon, preferably in methylene chloride and adding a tertiary amine base preferably triethylamine, the solution is cooled to 0° to 5° C. and, depending on the number of hydroxyl groups to be acetylated, a smaller or greater excess, in relation to the equivalent amount of an alkanecarboxylic acid anhydride or alkanecarboxylic acid chloride, e.g. preferably acetyl chloride is portionwise added to the solution in such a way that the temperature remains below 10° C. Subsequently, the temperature of the reaction mixture is increased to and maintained at room temperature until the reaction becomes complete. When not all the hydroxyl groups of the molecule are acylated, the progress of reaction is preferably followed by TLC to avoid any undesired acylation. Then the excess of acylating agent is decomposed by adding water and the solution is washed with dilute aqueous sodium hydroxide solution, followed by water, until it becomes acid free. After evaporation of the solvent the product obtained is purified by using chromatography or recrystallization or both.

Alternatively, the compounds of formula (IIa) may be prepared in such a way that formula (IIIa) containing >CR³R⁴ group as Z², wherein R³ and R⁴ together represent a C$_{2-5}$ alkylenedioxy group is hydrolyzed by boiling in dioxane in the presence of an acid, to obtain the corresponding derivative of formula (IIIa) containing >C=O group as Z², then after completion of the reaction, making the pH of the solution alkaline and evaporating dioxane, the residue is filtered after thoroughly triturating with water, the precipitate is washed with water until free from mother liquor, then dried and recrystallized. Subsequently, the compound of formula (IIIa) obtained is acylated on one or more of its hydroxyl group(s) as described above.

It is also possible that a compound of formula (IIIa) containing >C=O group as Z² is reduced if desired, before or after acylation preferably by using a complex metal hydride, suitably an alkaline metal borohydride in an alcohol, advantageously in methanol or in an ether-type solvent, preferably tetrahydrofuran or a halogenated hydrocarbon solvent, e.g. methylene chloride or in a mixture of the above solvents, suitably in methanol at a temperature between −10° C. and 10° C.

If desired, the hydroxyl group formed by reduction may also be acylated as described above.

Quaternary derivatives of the compounds of formula (IIa) obtained after acylation are prepared in such a way that the compound of formula (IIa) is dissolved in an inert solvent, e.g. acetonitrile, methylene chloride or an ether-type solvent, such as diethyl ether or in a ketone solvent, preferably acetone and then reacted suitably in the same solvent with an alkyl halide, e.g. with an acetone solution of methyl bromide or allyl bromide. The reaction mixture is allowed to stand until the reaction becomes complete, then the precipitate is filtered, washed until it becomes free from mother liquor and then purified.

When the quaternary salt formed does not crystallize from the solution it is precipitated by adding diethyl ether.

According to process b) a 17β-halo-2α,3α:16α,17α-diepoxy-5α-androstane derivative of formula (VI) is reacted with an amine of formula (VII), e.g. with the corresponding 1,4-dioxa-8-azaspiro[4.5]decane or 4-hydroxypiperidine, suitably in an inert solvent, preferably in acetonitrile, at room temperature. After the reaction has become complete, the reaction mixture is evaporated and the residue is diluted with water. After compacting, the precipitate is filtered, washed with water to remove mother liquor, dried and purified by recrystallization. The novel product of formula (V) obtained, which contains an α-aminoketone grouping in the ring D of the steroid skeleton, is reduced at its 17-oxo group by using an alkaline metal borohydride, suitably sodium borohydride in an inert solvent, e.g. tetrahydrofuran, methylene chloride, methanol or in a mixture of the above solvents, preferably methanol. After decomposing the complex metal hydride and evaporating the solvent, e.g. methanol, the product is obtained as a precipitate. After filtering the precipitate and washing it with water to be free of mother liquor, the product is dried and then recrystallized.

The compounds of formula (IVb) thus obtained are transformed to compounds of formula (I) through substances of formulae (IIIb) and (IIb) by using the chemical reaction given for the compounds of formula (IVa).

The salts of the quaternary derivatives formed with non-toxic mineral or organic acids are preferably obtained by dissolving the quaternary compound in ethanol, adding any of the above acids to the solution and precipitating the salt by adding ether.

The biological effectivity of the novel androstane derivatives of formula (I) substituted by a quaternary amino group in the 16-position was studied as described hereinafter.

The in vitro experiments were carried out on the phrenic nerve-(nervus phrenicus)-hemidiaphragm preparation of 300 to 350 g body weight (BW) rats or 400 to 500 g BW guinea-pigs. The phrenic nerve was stimulated with supramaximal electric impulses of 0.2 ms duration, administered at 0.1 Hz and the isometric contractions of the muscle were continuously registered. The preparations were suspended (kept) in 50 ml organ baths in physiological Krebs' solution. The composition of the solution was: 113 mmol/l sodium chloride, 4.7 mmol/l potassium chloride, 1.5 mmol/l calcium chloride, 0.2 mmol/l potassium dihydrophosphate, 1.2 mmol/l magnesium sulphate, 25 mmol/l sodium hydrocarbonate and 11.5 mmol/l glucose). The Krebs' solution was aerated with a mixture of 95% $O_2$-5% $CO_2$. The concentrations of the compounds to be tested were increased cumulatively and their $ED_{50}$ and $ED_{90}$ values (i.e. concentrations that decreased the force/magnitude/ of the contractions of the muscle/hemidiaphragm/by 50% and 90%, respectively) were determined. Since we found in earlier experiments, that the effects of muscle relaxants in guinea-pigs are similar to those observed in clinical practice in man, we compared the effects of our compounds with those of other non-depolarizing muscle relaxants in this species. In the in vivo experiments guinea-pigs were anesthetized with a mixture of pentobarbital [5-ethyl-5-(1-methylbutyl)-2,4,6-(1H,3H,5H)-pyrimidinetrione] and urethane [ethyl carbamate] and were mechanically ventilated with oxygen. The tibialis anterior muscle was isolated (prepared), the sciatic nerve (nervus ischiadicus) was stimulated electrically (supramaximal stimuli of 0.2 ms duration, administered at 0.1 Hz) and the contractions of the muscle were registered. The inhibiting effect of the compounds on the vagus nerve was investigated on cats anesthetized with a mixture of chloralose (condensation product of chloral hydrate and glucose) and urethane. The vagus nerve was electrically (supramaximal stimuli of 0.3 ms duration, administered at 20 Hz) stimulated and the effect on heart rate and blood pressure was recorded on a Hellige recorder. All compounds were administered through a jugular vein. The experimental results are summarized in the ensuring tables (Tables 1 to 4).

TABLE 1

In vitro muscle relaxing effect on the isolated phrenic nerve-hemidiaphragm preparation of rats and guinea-pigs, respectively (0.1 Hz, 0.2 ms, supramaximal stimulus). Mean ± SEM (n = 4).

| Compound | $ED_{90}$ (μmol/l) rat | $ED_{90}$ (μmol/l) guinea-pig |
| --- | --- | --- |
| Tuburcurarine chloride (d-Tubocurarine)*[1] | 1.02 ± 0.01 | 1.33 ± 0.09 |
| Pancuronium bromide | 6.36 ± 0.03 | 0.29 ± 0.01 |
| Vecuronium bromide | 8.72 ± 0.38 | 0.25 ± 0.01 |
| Pipecuronium bromide | 1.50 ± 0.04 | 0.08 ± 0.003 |
| Compound of Example 8 | 8.37 ± 0.26 | 0.90 ± 0.03 |

Note:
*[1] The chemical name of tubocurarine (d-tubocurarine) is 7',12'-dihydroxy-6,6'-dimethoxy-2,2',2'-trimethyltubocuraranium chloride hydrochloride.

The data of Table 1 indicate that the neuromuscular blocking (inhibitory) effect of 1-[3α,17β-bis(acetyloxy)-2β-(1,4-dioxa-8-azaspiro[4.5]dec-8-yl)-5α-androstan-16β-yl]-1-(2-propenyl)pyrrolidinium bromide of Example 8, on both rats and guinea-pigs, is of the similar order of magnitude as that of other known, clinically employed muscle relaxants. The onset of action of the compound of Example 8 was rapid and was easily reversible by wash-out. The effect could also be antagonized with neostigmine methyl sulfate [(3-dimethylcarbamoxyphenyl)trimethylammoniummethyl sulfate] or edrophonium chloride [ethyl-(3-hydroxyphenyl)dimethylammonium chloride].

TABLE 2

In vivo effect determined on the anterior tibial muscle (musculus tibialis anterior) of the guinea-pig. Mean ± SEM (n = 4).

| Compound | $ED_{50}$ (μg/kg) | $ED_{90}$ (μg/kg) | Onset time (min)*1) | Clinical duration (min)*2) | Recovery 25%–75% (min)*3) |
|---|---|---|---|---|---|
| Pancuronium bromide | 10 ± 1.1 | 15 ± 1.9 | 1.1 ± 0.31 | 45.6 ± 5.68 | 14.8 ± 2.45 |
| Vecuronium bromide | 7 ± 1.9 | 11 ± 2.0 | 1.3 ± 0.51 | 26.6 ± 4.61 | 9.0 ± 2.35 |
| Pipecuronium bromide | 4 ± 0.7 | 6 ± 0.7 | 1.5 ± 0.08 | 60.6 ± 9.28 | 24.6 ± 3.71 |
| Compound of Example 8 | 34 ± 2.0 | 48 ± 2.7 | 0.9 ± 0.18 | 10.1 ± 1.32 | 2.4 ± 0.3 |

Note:
*1)Time required to 95% block (effect), when administered in 2 × $ED_{90}$ dose.
*2)The decrease to 75% of the blocking effect of the compound administered in 2 × $ED_{90}$ dose.
*3)Time required to the decrease of 75% blocking effect to 25%.

The data of Table 2 indicate that in in vivo experiments, on guinea-pigs the onset of action of the compound, Example 8, was more rapid and its duration of action was shorter than those of other reference substances with similar chemical structure. Thus, for example, after its administration in 2×$ED_{90}$ doses the 75% neuromuscular block decreased to 25% in 10.1 min. Comparable values for pancuronium bromide and pipecuronium bromide were 45.6 and 60.6 min respectively.

TABLE 3

Investigation of the antivagal effect on anesthetized cat. Mean ± SEM (n = 4).

| | Decrease in heart rate (%) | Decrease in blood pressure (Hgmm) |
|---|---|---|
| Control | 14 ± 1.8 | 40.0 ± 8.1 |
| Compound of Example 8 | 15 ± 2.9 | 32.0 ± 6.6 |

TABLE 4

Comparison of the effects of 2 × $ED_{90}$ doses in beagle dog (no. of animals in parentheses). Mean ± SEM.

| | Compound of Example 8 | Vercuronium bromide | P |
|---|---|---|---|
| Time (sec) to 80% block (8) | 48.4 ± 2.9 | 62.8 ± 4.5 | <0.01 |
| Onset time (sec) (8) | 75.3 ± 5.9 | 115.1 ± 8.6 | <0.001 |
| Clinical duration (min) (8) | 12.6 ± 0.6 | 17.8 ± 1.1 | <0.001 |
| Recovery index (min) (4) | 3.4 ± 0.4 | 6.6 ± 1.1 | <0.02 |
| Recovery 0–75% (min) (4) | 16.2 ± 0.9 | 24.9 ± 3.0 | <0.02 |
| Time to max. recovery (min) (4) | 24.4 ± 2.0 | 31.4 ± 4.3 | <0.02 |
| $T_4/T_1$ at max. recovery (4) | 91.3 ± 4.8 | 71.0 ± 2.9 | <0.05 |
| Tetanic fade (min) (4) | 97.5 ± 1.9 | 95.5 ± 4.5 | n.s. |
| $ED_{50}$ (μg/kg) (8) | 7.0 ± 0.1 | 22.6 ± 0.5 | |
| $ED_{90}$ (μg/kg) (8) | 10.5 ± 0.2 | 35.8 ± 0.9 | |
| $ED_{95}$ (μg/kg) (8) | 11.1 ± 0.2 | 37.9 ± 1.0 | |

Note:
In the column "P", abbreviation "n.s." means "not significant".

It is known that some non-depolarizing muscle relaxants have unwanted side effects and because of their inhibitory effect on the vagus and or their histamine releasing effect may cause tachycardia and decrease of blood pressure (W. C. Bowman: Pharmacology of Neuromuscular Function, pp. 99–105, Wright, London, 1980). These adverse side effects may limit the clinical use of such compounds. The data on Table 3 demonstrate that, in in vivo cat experiments, compound of Example 8 , has no stimulating effect on the vagus and its electrical stimulation causes no significant change in heart rate or blood pressure. While the 4×$ED_{90}$ dose of pancuronium bromide caused a 50% inhibition of the decrease of heart rate and blood pressure caused by vagal stimulation (see Bowman's publications cited above), even the 8×$ED_{90}$ dose of compound of Example 8 did not block the vagus, and did not inhibit the effects of electrical stimulation of this nerve on heart rate or blood pressure.

The compounds of formula (I) are curate-like neuromuscular blocking agents possessing a non-depolarizing mechanism of action; i.e. they inhibit the transmission of nerve impulse to striated muscle. They do not induce histamine release or hypotension and their effect can be antagonized by neostigmine. They have no hormonal side effect. The rapid onset and short duration of their effect represent further (additional) advantages and result in the rapid recovery of normal neurotransmission after discontinuation of their administration.

The compounds of formula (I) can be employed primarily in surgery to produce muscle relaxation during endotracheal anesthesia. They can be used for the prevention of trauma in electroshock therapy and for the decreasing muscle tone in spastic conditions, etc.

The novel androstane derivatives of formula (I) substituted with a quaternary amino group in 16-position are used as bases, or in the form of their salts, suitably in formulations (compositions) commonly employed in clinical practice. These compositions may be formulated to be suitable for intravenous injection or infusion, primarily in lyophilized form in powder ampoules. Common filling, diluting, preserving, pH or osmotic-pressure influencing (tonicizing) additives and auxiliaries may be employed in the preparation of these compositions. From the pharmacological composition, the amount of the active agent, required to obtain the desired effect, is administered to the patient. This dose depends on the desired effect, the body weight and the sensitivity of the patient to the active agent. The dose of active agent to be administered is determined by physician familiar with the patients condition and with the pharmacological properties of the compound.

For the sake of easy administration, it is advisable to formulate the pharmaceutical compositions in dosage units which contain a single dose or multiples, or one half, one third or one quarter of the single dose.

According to the invention the pharmaceutical compositions contain 1 to 100 mg of the active agent in one dosage unit (ampoule). Naturally, it is conceivable that, in some cases, the amount of active agent may be higher or lower than the above limits.

The invention also relates to a method for blocking the transmission of nerve impulses (stimuli) to striated muscles. This involves the administration of a therapeutically effective dose of the active agent of formula (I) or a pharmaceutically acceptable salt of the bases (I) to mammals (including man).

The thin layer chromatography examinations were carried out on DC-Alufolien Kieselgel 60 adsorbent (Merck, Art. 5553, of 0.2 mm size) by detecting with iodine. The eluents used were:

1: a 9:1 v/v mixture of chloroform and methanol;
2: a 7:3 v/v mixture by volume of chloroform with methanol; and
3: an 1:1 v/v mixture of benzene with acetone. The eluent was indicated as an index in the Rf values given in the Examples.

The invention is illustrated in detail by the aid of the following non-limiting Examples.

EXAMPLE 1

Preparation of 2α,3α-epoxy-16β-(1-pyrrolidinyl)-5α-androstane-17-one

To a suspension containing 60 g of 17-bromo-2α,3α:16α,17α-diepoxy-5α-androstane in 400 ml acetonitrile, 42 ml of pyrrolidine are added at room temperature while vigorous stirring and introducing gaseous nitrogen. After stirring for 5 minutes the suspension becomes clear while the temperature of the reaction mixture reaches 50° C. During the progress of the reaction the precipitation of product begins. After completion of the reaction mixture is evaporated, water is added to the residue, the precipitate is filtered, thoroughly washed with water and dried to give 55.9 g of the title product, which is recrystallized from methanol, m.p.: 167°–169° C.

EXAMPLE 2

Preparation of 2α,3α-epoxy-16β-(1-pyrrolidinyl)-5α-androstane-17β-ol

After dissolving 39.2 g of 2α,3α-epoxy-16β-(1-pyrrolidinyl)-5α-androstan-17-one in a mixture of 392 ml of methanol and 56 ml of methylene chloride. 14.7 g Sodium borohydride are portionwise added while stirring and introducing nitrogen at such a rate that the temperature reaches room temperature as a maximum. The solution containing a precipitate is left to stand for 12 hours, then methylene chloride is evaporated, and the residue is diluted with water. The precipitate is filtered, thoroughly washed with water, dried and recrystallized from methanol to obtain the title product in a yield of 33.3 g (89.5%), m.p.: 167°–169° C.

EXAMPLE 3

Preparation of 2β-(1,4-dioxa-8-azaspiro[4.5]dec-8-yl)-16β-(1-pyrrolidinyl)-5α-androstane-3α,17β-diol After adding 63 g of 1,4-dioxa-8-azaspiro[4.5]decane and 13 ml of water to 17 g of 2α,3α-epoxy-16β-(1-pyrrolidinyl)-5α-androstane-17β-ol, the reaction mixture is maintained at 100° to 105° C. for 80 hours while introducing nitrogen. After completion of the reaction, the solution containing a precipitate is diluted with 200 ml of acetonitrile and after filtering, the precipitate is thoroughly washed with water and then with acetonitrile, dried and recrystallized from methanol to give the title product in a yield of 18.2 g (76.5%), m.p.: 184°–187° C.

EXAMPLE 4

Preparation of 2β-(1,4-dioxa-8-azaspiro[4.5]dec-8-yl)-16β-(1-pyrrolidinyl)-5α-androstane-3α,17β-diol-17-acetate After dissolving 10 g of 2β-(1,4-dioxa-8-azaspiro-[4.5]dec-8-yl)-16β-(1-pyrrolidinyl)-5α-androstane-3α,17β-diol in 50 ml of methylene chloride 3.5 ml of triethylamine are added. The solution is cooled to 0° C. and 2.5 ml of acetyl chloride are dropwise added while maintaining the temperature between 0° and 5° C. Thereafter, the reaction mixture is allowed to warm to room temperature and maintained at the same temperature for 3 hours. After completion of the reaction, the excess of acetyl chloride is decomposed by adding water and the methylene chloride solution is washed first with sodium hydroxide solution, then with water. After separation, the organic phase is dried over anhydrous sodium sulfate and after filtering the drying agent methylene chloride is evaporated. The residue is purified on silica gel column and recrystallized from acetone to yield 7.19 g (65.4%), m.p.: 174°–177° C.

EXAMPLE 5

Preparation of 1-[17β-Acetyloxy-2β-(1,4-dioxa-8-azaspiro[4.5]dec-8-yl)-3α-hydroxy-5α-androstan-16β-yl]-1-(2-propenyl)pyrrolidinium bromide After dissolving 1.5 g of 2β-(1,4-dioxa-8-azaspiro[4.5]dec-8-yl)-16β-(1-pyrrolidinyl)-5α-androstane-3α,17β-diol-17-acetate in 30 ml of acetone, 2.5 ml of allyl bromide are added, the reaction mixture is kept for 24 hours, then the product is precipitated by ether, filtered and recrystallized from acetone to give the title product in a yield of 1.4 g (76.5%), m.p.: 178°–180° C.

$^1$H-NMR:300 MHz (CDCl$_3$) δ ppm: 0.82 (s, 6H, 18-CH$_3$ and 19-CH$_3$), 2.24 (s, 3H, 17-OAc), 2.44–2.8 (m, 5H, 2α-H and NCH$_2$), 3.6–4.1 (m, 5H, 3β-H and N$^+$CH$_2$), 3.96 (s, 4H, CH$_2$O), 4.18 and 4.42 (m, 2H, $N^+CH_2$—CH=), 4.55 (vbr, 1H, 16α-H), 5.22 (d, 1H, 17α-H), 5.66–5.80 (m, 2H, =CH$_2$), 6.17 (m, 1H, —CH=).

EXAMPLE 6

Preparation of 2β-(1,4-dioxa-8-azaspiro[4.5]dec-8-yl)-16β-(1-pyrrolidinyl)-5α-androstane-3α,17β-diol-diacetate To a solution containing 10 g of 2β-(1,4-dioxa-8-azaspiro[4.5]dec-8-yl)-16β-(1-pyrrolidinyl)-5α-androstane-3α,17β-diol in 50 ml of methylene chloride, 7 ml of triethylamine are added and the solution is cooled to 0° C. To this solution 4.4 ml of acetyl chloride are dropwise added while cooling and stirring at such a rate that the temperature remains below 10° C. After termination of the addition the cooling is stopped and the mixture is allowed to warm to room temperature. The complete reaction requires about 16 hours. Thereafter, the excess of acetyl chloride is decomposed by adding water and the methylene chloride solution is washed with aqueous sodium hydroxide solution and then with water until neutral. The methylene chloride phase is dried, evaporated and the residue is purified on a silica gel column to yield 9 g (77.1%) of the title product as a foam.

$^1$H-NMR:300 MHz (CDCl$_3$) δ ppm: 0.87 (s, 3H, 18-CH$_3$), 0.99 (s, 3H, 19-CH$_3$), 2.06 and 2.11 (s, s, 3H, 3H, 3-OAc and 17-OAc), 2.42 (q, 1H, 2α-H), 2.92 (q, 1H, 16α-H), 3.93 (s, 4H, CH$_2$O), 4.80 (d, 1H, 17α-H), 5.24 (q, 1H, 3β-H).

EXAMPLE 7

Preparation of 1-[3α,17β-bis(acetyloxy)-2β-(1,4-dioxa-8-azaspiro[4.5]dec-8-yl)-5α-androstan-16β-yl]-1-methylpyrrolidinium bromide After dissolving 1 g of 2β-(1,4-dioxa-8-azaspiro[4.5]dec-8-yl)-16β-(1-pyrrolidinyl)-5α-androstane-3α,17β-dioldiacetate in 20 ml of diethyl ether and adding 2.5 ml of a 10% solution of methyl bromide in acetone, the reaction mixture is left to stand 48 hours. After filtering, the precipitate is recrystallized from a mixture of acetone and diethyl ether to obtain the title product in a yield of 1.00 g (82%), m.p.: 167°–170° C.

$^1$H-NMR:300 MHz (CDCl$_3$) δ ppm: 0.82 (s, 6H, 18-CH$_3$), 1.00 (s, 3H, 19-CH$_3$), 2.06 (s, 3H, 3-OAc), 2.23 (s, 3H, 17-OAc), 2.61 (br, 4H, NCH$_2$), 3.30 (s, 3H, N$^+$CH$_3$), 3.65–4.1 (m, 4H, N$^+$CH$_2$), 3.94 (s, 4H, OCH$_2$CH$_2$O), 4.75 (m, 1H, 16α-H), 5.24 (m, 1H, 3β-H), 5.26 (d, 1H, 17α-H).

EXAMPLE 8

Preparation of 1-[3α,17β-bis(acetyloxy)-2β-(1,4-dioxa-8-azaspiro[4.5]dec-8-yl)-5α-androstan-16β-yl]-1-(2-propenyl)pyrrolidinium bromide After adding 20 ml of allyl bromide to a solution containing 13 g of 2β-(1,4-dioxa-8-azaspiro[4.5]dec-8-yl)-16β-(1-pyrrolidinyl)-5α-androstane-3α,17β-diol-diacetate in 100 ml of acetone, the reaction mixture is kept for 24 hours at room temperature. After completion of the reaction, the product is precipitated by ether, filtered, washed with a mixture of ether and acetone until it becomes free from allyl bromide and dried. The quaternary compound (13.4 g) thus obtained is purified by chromatography on a silica gel column. After evaporating the combined fraction containing the aimed product, the residue is recrystallized from a mixture of acetone and ether to obtain the title product in a yield of 9 g (55.8%), m.p.: 186°–189° C.

$^1$H-NMR:300 MHz (CDCl$_3$) δ ppm: 0.81 (s, 3H, 18-CH$_3$), 0.99 (s, 3H, 19-CH$_3$), 2.07 (s, 3H, 3-OAc), 2.23 (s, 3H, 17-OAc), 3.75–4.1 (m, 4H, N$^+$CH$_2$), 3.94 (s, 4H, OCH$_2$CH$_2$O), 4.18 and 4.38 (m, 2H, N$^+$CH$_2$—CH=), 4.65 (vbr, 1H, 16α-H), 5.22 and 5.24 (m, 2H, 3β-H and 17α-H), 5.66–5.80 (m, 2H, =CH$_2$), 6.17 (m, 1H, —CH=).

EXAMPLE 9

Preparation of 2β-(4-oxo-1-piperidinyl)-16β-(1-pyrrolidinyl)-5α-androstane-3α,17β-diol After adding 42 ml of 10% aqueous hydrochloric acid solution to 5 g of 2β-(1,4-dioxa-8-azaspiro[4.5]dec-8-yl)-16β-(1-pyrrolidinyl)-5α-androstane-3α,17β-diol dissolved in 100 ml of dioxane, the reaction mixture is boiled under reflux for 3 hours. After completion of the reaction, the solution is made alkaline by adding aqueous sodium hydroxide solution, dioxane is distilled off and the residue is diluted with water. After filtering, the precipitate is washed with water until neutral and dried. The crude product is dissolved in acetonitrile, clarified by activated carbon and after filtering off the adsorbent, two thirds of acetonitrile are distilled off. After filtering, the crystalline precipitate is dried to give the title product in a yield of 4.2 g (92.1%), m.p.: 136°–138° C.

EXAMPLE 10

Preparation of 2β-(4-oxo-1-piperidinyl)-16β-(1-pyrrolidinyl) 5α-androstane-3α,17β-diol-17-acetate 2β-(1,4-Dioxa-8-azaspiro[4.5]dec-8-yl)-16β-(1-pyrrolidinyl)-5α-androstane-3α,17β-diol is acetylated as described in Example 4 to obtain the title product in a yield of 53.8%, m.p.: 190°–192° C.

EXAMPLE 11

Preparation of 2β-(4-hydroxy-1-piperidinyl)-16β-(1-pyrrolidinyl)-5α-androstane-3α,17β-diol-17-acetate After portionwise adding at 0° C. 0.8 g of sodium borohydride to a solution containing 2 g of 2β-(4-oxo-1-piperidinyl)-16β-(1-pyrrolidinyl)-5α-androstane-3α,17β-diol-17-acetate in the mixture of 10 ml methylene chloride and 10 ml of methanol, the reaction mixture is vigorously stirred for 3 hours. After completion of the reaction, the excess of reagent is decomposed by water and after evaporating methylene chloride, the residue is thoroughly triturated with water, filtered and dried. The product is obtained in a yield of 1.3 g (64.7%), m.p.: 206°–209° C.

EXAMPLE 12

Preparation of 1-[17β-acetyloxy-3α-hydroxy-2β-(4-hydroxy-1-piperidinyl)-5α-androstan-16β-yl]-1-methylpyrrolidinium bromide 2β-(4-Hydroxy-1-piperidinyl)-16β-(1-pyrrolidinyl)-5α-androstane-3α,17β-diol-17-acetate is reacted with methyl bromide as described in Example 7 to give the title compound in a yield of 93.6%, m.p.: 262°–264° C.

$^1$H-NMR:300 MHz (DMSO-d$_6$) δ ppm: 0.77 (s, 3H, 18-CH$_3$), 0.96 (s, 3H, 19-CH$_3$), 2.19 (s, 3H, 17-OAc), 3.09 (s, 3H, N$^+$CH$_3$), 3.96 (m, 1H, 3β-H), 4.15 (m, 1H, 16α-H), 5.08 (d, 1H, 17α-H).

EXAMPLE 13

Preparation of 1-[17β-acetyloxy-3α-hydroxy-2β-(4-hydroxy-1-piperidinyl)-5α-androstan-16β-yl]-1-(2-propenyl)pyrrolidinium bromide 2β-(4-Hydroxy-1-piperidinyl)-16β-(1-pyrrolidinyl)-5α-androstane-3α,17β-diol-17-acetate is reacted with allyl bromide as described in Example 5 to obtain the title compound in a yield of 74.6%, m.p.: 227°–232° C.

EXAMPLE 14

Preparation of
2β-(4-oxo-1-piperidinyl)-16β-(1-pyrrolidinyl)-
5α-androstane-3α,17β-diol-diacetate 2β-(4-Oxo-1-piperidinyl)-16β-(1-pyrrolidinyl)-5α-androstane-3α,17β-diol is acetylated as described in Example 6 to give the foam-like title compound in a yield of 62%, $R_f^1$=0.34.

EXAMPLE 15

Preparation of 2β-(4-hydroxy-1-piperidinyl)-
16β-(1-pyrrolidinyl)-5α-androstane-
3α,17β-diol-diacetate 2β-(4-Oxo-1-piperidinyl)-16β-(1-pyrrolidinyl)-5α-androstane-3α,17β-diol-diacetate is reduced by sodium borohydride as described in Example 11 to give the foam-like title compound in a yield of 81%, $R_f^2$=0.55.

EXAMPLE 16

Preparation of
1-[3α,17β-bis(acetyloxy)-2β-(4-hydroxy-
1-piperidinyl)-5α-androstan-16β-yl]-
1-(2-propenyl)pyrrolidinium bromide 2β-(4-Hydroxy-1-piperidinyl)-16β-(1-pyrrolidinyl)-5α-androstane-3α,17β-diol-diacetate is reacted with allyl bromide as described in Example 5 to give the title compound in a yield of 93.28%.

$^1$H-NMR:300 MHz (CDCl$_3$) δ ppm: 0.82 (s, 3H, 18-CH$_3$), 1.00 (s, 3H, 19-CH$_3$), 2.08 (s, 3H, 3-OAc), 2.23 (s, 3H, 17-OAc), 3.55–4.1 (m, 5H, N$^+$CH$_2$ and hydroxypiperidine-4-H), 4.18 and 4.37 (m, 2H, N$^+$CH$_2$—CH=), 4.65 (vbr, 1H, 16α-H), 5.21 and 5.24 (m, 2H, 3β-H and 17α-H), 5.65–5.80 (m, 2H, =CH$_2$), 6.17 (m, 1H, —CH=).

EXAMPLE 17

Preparation of
2β-(4-hydroxy-1-piperidinyl)-16β-(1-pyrrolidinyl)-
5α-androstane-3α,17β-diol 2α,3α-Epoxy-16β-(1-pyrrolidinyl)-5α-androstane-17β-ol is reacted with 4-hydroxypiperidine as described in Example 3 to obtain the title product in a yield of 76.5%, m.p.: 188°–190° C.

EXAMPLE 18

Preparation of 2β-(4-acetyloxy-1-piperidinyl)-
16β-(1-pyrrolidinyl)-5α-androstane-
3α,17β-diol-diacetate After adding 7.9 g of triethylamine to a solution containing 9 g of 2β-(4-hydroxy-1-piperidinyl)-16β-(1-pyrrolidinyl)-5α-androstane-3α,17β-diol in 80 ml of methylene chloride, 9 g of acetyl chloride are dropwise added to the solution at a temperature of 0° C. under cooling and stirring. After termination of the addition, the reaction mixture is maintained at room temperature for 24 hours. After completion of the reaction the excess of acetyl chloride is decomposed by water, the methylene chloride solution is washed with aqueous sodium hydroxide solution until it becomes acid-free, then washed with water several times until neutral. After drying the methylene chloride solution and evaporating, the residue is purified on a silica gel column to yield 8.3 g (71.9%) of the title compound, $R_f^1$=0.36.

EXAMPLE 19

Preparation of
1-[3α,17β-bis(acetyloxy)-2β-(4-acetyloxy-
1-piperidinyl)-5α-androstan-16β-yl]-
1-methylpyrrolidinium bromide 2β-(4-Acetyloxy-1-piperidinyl)-16β-(1-pyrrolidinyl)-5α-androstane-3α,17β-diol-diacetate is reacted with methyl bromide as described in Example 7 to obtain the title compound in a yield of 79.7%, m.p.: 160°–180° C.

EXAMPLE 20

Preparation of
2β-(1,4-dioxa-8-azaspiro[4.5]dec-8-yl)-3α,
17β-dihydroxy-16β-(1-piperidinyl)-5α-androstane 2α,3α-Epoxy-16β-(1-piperidinyl)-5α-androstane-17β-ol is reacted with 1,4-dioxa-8-azaspiro[4.5]decane as described in Example 3 to give the title compound in a yield of 79.88%, m.p.: 216°–218° C.

EXAMPLE 21

Preparation of
2β-(4-oxo-1-piperidinyl)-16β-(1-piperidinyl)-
5α-androstane-3α,17β-diol 2β-(1,4-Dioxa-8-azaspiro[4.5]dec-8-yl)-16β-(1-piperidinyl)-5α-androstane-3α,17β-diol is hydrolyzed by following the procedure described in Example 9 to yield 81.66%, m.p.: 205°–206° C.

EXAMPLE 22

Preparation of
2β-(4-oxo-1-piperidinyl)-16β-(1-piperidinyl)-
5α-androstane-3α,17β-diol-17-acetate 2β-(4-Oxo-1-piperidinyl)-16β-(1-piperidinyl)-5α-androstane-3α,17β-diol is acetylated as described in Example 4 to obtain the title compound in a yield of 60.5%, m.p.: 204°–207° C.

$^1$H-NMR:300 MHz (CDCl$_3$) δ ppm: 0.80 (s, 3H, 18-CH$_3$), 0.86 (s,3H, 19-CH$_3$), 2.09 (s, 3H, 17-OAc), 3.06 (m, 1H, 16α-H), 3.89 (m, 1H, 3β-H), 4.77 (d, 1H, 17α-H).

EXAMPLE 23

Preparation of
2β-(4-hydroxy-1-piperidinyl)-16β-(1-piperidinyl)-
5α-androstane-3α,17β-diol-17-acetate 2β-(4-Oxo-1-piperidinyl)-16β-(1-piperidinyl)-5α-androstane-3α,17β-diol-17-acetate is reduced by using sodium borohydride as described in Example 11 to obtain the title compound in a yield of 92.4%, m.p.: 202°–204° C.

EXAMPLE 24

Preparation of
1-[17β-acetyloxy-3α-hydroxy-2β-(4-hydroxy-
1-piperidinyl)-5α-androstan-16β-yl]-
1-methylpiperidinium bromide 2β-(4-Hydroxy-1-piperidinyl)-16β-(1-piperidinyl)-5α-androstane-3α,17β-diol-17-acetate is reacted with methyl bromide as described in Example 7 to give the title compound in a yield of 82.97%, m.p.: 238°–240° C.

$^1$H-NMR:300 MHz (DMSO-d$_6$) δ ppm: 0.75 (s, 3H, 18-CH$_3$), 0.96 (s, 3H, 19-CH$_3$), 2.18 (s, 3H, 17-OAc), 3.13 (s, 3H, N$^+$CH3), 3.96 (m, 1H, 3β-H), 4.29 (m, 1H, 16α-H), 5.14 (d, 1H, 17α-H).

EXAMPLE 25

Preparation of
2β-(4-oxo-1-piperidinyl)-16β-(1-piperidinyl)-
5α-androstane-3α,17β-diol-diacetate 2β-(4-Oxo-1-piperidinyl)-16β-(1-piperidinyl)-5α-androstane-3α,17β-diol is acetylated as described in Example 6 to obtain the title product in a yield of 61.05%, m.p.: 179°–181° C.

$^1$H-NMR:300 MHz (CDCl$_3$) δ ppm: 0.82 (s, 3H, 18-CH$_3$), 1.05 (s, 3H, 19-CH$_3$), 2.09 and 2.12 (s, s, 3H, 3H, 3-OAc and 17-OAc), 3.1 (m, 1H, 16α-H), 4.83 (d, 1H, 17α-H), 5.30 (m, 1H, 3β-H).

EXAMPLE 26

Preparation of
2β-(4-hydroxy-1-piperidinyl)-16β-(1-piperidinyl)-
5α-androstane-3α,17β-diol-diacetate 2β-(4-Oxo-1-piperidinyl)-16β-(1-piperidinyl)-5α-androstane-3α,17β-diol-diacetate is reduced by using sodium borohydride as described in Example 1 to give the title compound in a yield of 69.5%, m.p.: 108°–110° C.

$^1$H-NMR:300 MHz (CDCl$_3$) δ ppm: 0.81 (s, 3H, 18-CH$_3$), 1.03 (s, 3H, 19-CH$_3$), 2.08 and 2.12 (s, s, 3H, 3H, 3-OAc and 17-OAc), 3.65 (m, 1H, hydroxypiperidine-4-H), 4.81 (d, 1H, 17α-H), 5.28 (m, 1H, 3β-H).

EXAMPLE 27

Preparation of
1-[3α,17β-bis(acetyloxy)-2β-(4-hydroxy-
1-piperidinyl)-5α-androstan-16β-yl]-
1-methylpiperidinium bromide 2β-(4-Hydroxy-1-piperidinyl)-16β-(1-piperidinyl)-5α-androstane-3α,17β-diol-diacetate is reacted with methyl bromide as described in Example 7 to obtain the title compound in a yield of 68.4%, m.p.: 220°–230° C. (with decomposition).

$^1$H-NMR:300 MHz (CDCl$_3$) δ ppm: 0.83 (s, 3H, 18-CH$_3$), 1.02 (s, 3H, 19-CH$_3$), 2.09 (s, 3H, 3-OAc), 2.22 (s, 3H, 17-OAc), 3.41 (s, 3H, N$^+$CH$_3$), 5.15–5.55 (m, 2H, 3β-H and 17α-H).

EXAMPLE 28

Preparation of
2β-(1,4-dioxa-8-azaspiro[4.5]dec-8-yl)-3α,
17β-dihydroxy-16β-(4-methyl-1-piperazinyl)-
5α-androstane 2α,3α-Epoxy-17β-hydroxy-16β-(4-methyl-1-piperazinyl)-5α-androstane is reacted with 1,4-dioxa-8-azaspiro[4.5]decane as described in Example 3 to give the title compound in a yield of 72.34%, m.p.: 185°–187° C.

EXAMPLE 29

Preparation of
2β-(1,4-dioxa-8-azaspiro[4.5]dec-8-yl)-
16β-(4-methyl-1-piperazinyl)-5α-androstane-
3α,17β-diol-diacetate 2β-(1,4-Dioxa-8-azaspiro[4.5]dec-8-yl)-16β-(4-methyl-1-piperazinyl)-5α-androstane-3α,17β-diol is acetylated as described in Example 6 to give the title compound in a yield of 70%, m.p.: 162°–165° C.

EXAMPLE 30

Preparation of 4-[3α,17β-bis(acetyloxy)-2β-
(1,4-dioxa-8-azaspiro[4.5]dec-8-yl)-
5α-androstan-16β-yl]-1,1-dimethylpiperazinium
bromide 2β-(1,4-Dioxa-8-azaspiro[4.5]dec-8-yl)-16β-(4-methyl-1-piperazinyl)-5α-androstane-3α,17β-diol-diacetate is reacted with methyl bromide as described in Example 7. The reaction becomes complete after 5 hours. The title compound is obtained in a yield of 72%, m.p.: 244°–250° C.

$^1$H-NMR:300 MHz (CDCl$_3$) δ ppm: 0.77 (s, 3H, 18-CH$_3$), 1.00 (s, 3H, 19-CH$_3$), 2.06 (s, 3H, 3-OAc), 2.11 (s, 3H, 17-OAc), 2.44 (m, 1H, 2α-H), 2.61 (br, 4H, NCH$_2$), 2.8–3.05 (m, 4H, NCH$_2$), 3.23 (m, 1H, 16α-H), 3.56 (s, 6H, N$^+$CH$_3$), 3.60 and 3.70 (m, 4H, N$^+$CH$_2$), 3.93 (s, 4H, OCH$_2$CH$_2$O), 4.78 (d, 1H, 17α-H), 5.23 (m, 1H, 3β-H).

EXAMPLE 31

Preparation of
4-[3α,17β-bis(acetyloxy)-2β-(1,4-dioxa-
8-azaspiro[4.5]dec-8-yl)-5α-androstan-16β-yl]-
1-methyl-1-(2-propenyl)piperazinium bromide 2β-(1,4-Dioxa-8-azaspiro[4.5]dec-8-yl)-16β-(4-methyl-1-piperazinyl)-5α-androstane-3α,17β-diol-diacetate is reacted with allyl bromide as described in Example 5. The reaction becomes complete after 5 hours. The title product is obtained in a yield of 78%, m.p.: 205°–208° C.

$^1$H-NMR:300 MHz (CDCl$_3$) δ ppm: 0.77 (s, 3H, 18-CH$_3$), 1.00 (s, 3H, 19-CH$_3$), 2.06 (s, 3H, 3-OAc), 2.11 (s, 3H, 17-OAc), 2.44 (m, 1H, 2α-H), 2.62 (br, 4H, NCH$_2$), 2.8–3.05 (m, 4H, NCH$_2$), 3.23 (m, 1H, 16α-H), 3.43 (s, 3H, N$^+$CH$_3$), 3.4–3.85 (m, 4H, N$^+$CH$_2$), 3.93 (s, 4H, OCH$_2$CH$_2$O), 4.57 (m, 2H, N$^+$CH$_2$—CH═), 4.77 (d, 1H, 17α-H), 5.23 (m, 1H, 3β-H), 5.76 and 5.90 (2×dd, 2H, ═CH$_2$), 6.01 (m, 1H, —CH═).

EXAMPLE 32

Preparation of
16β-(4-methyl-1-piperazinyl)-2β-(4-oxo-
1-piperidinyl)-5α-androstane-3α,17β-diol 2β-(1,4-dioxa-8-azaspiro[4.5]dec-8-yl)-16β-(4-methyl-1-piperazinyl)-5α-androstane-3α,17β-diol is hydrolyzed according to the procedure described in Example 9 to obtain the title compound in a yield of 73.9%, m.p.: 225°–229° C.

$^1$H-NMR:300 MHz (CDCl$_3$) δ ppm: 0.68 (s, 3H, 18-CH$_3$), 0.88 (s, 3H, 19-CH$_3$), 2.29 (s, 3H, NCH$_3$), 3.43 (d, 1H, 17α-H), 3.9 (m, 1H, 3β-H).

EXAMPLE 33

Preparation of
16β-(4-methyl-1-piperazinyl)-2β-(4-oxo-
1-piperidinyl)-5α-androstane-3α,17β-diol-17-acetate 16β-(4-Methyl-1-piperazinyl)-2β-(4-oxo-1-piperidinyl)-5α-androstane-3α,17β-diol is acetylated as described in Example 4 to obtain the title compound in a yield of 77.34%, m.p.: 210°–215° C.

$^1$H-NMR:300 MHz (CDCl$_3$) δ ppm: 0.81 (s, 3H, 18-CH$_3$), 0.87 (s, 3H, 19-CH$_3$), 2.09 (s, 3H, 17-OAc), 2.25 (s, 3H, NCH$_3$), 3.9 (m, 1H, 3β-H), 4.75 (d, 1H, 17α-H).

EXAMPLE 34

Preparation of 2β-(4-hydroxy-1-piperidinyl)-
16β-(4-methyl-1-piperazinyl)-5α-androstane-3α,
17β-diol-17-acetate 16β-(4-Methyl-1-piperazinyl)-2β-(4-oxo-1-piperidinyl)-5α-androstane-3α,17β-diol-17-acetate is reduced by using sodium borohydride as described in Example 11 to obtain the title compound in a yield of 71%, m.p.: 210°–214° C.

$^1$H-NMR:300 MHz (CDCl$_3$) δ ppm: 0.81 (s, 3H, 18-CH$_3$), 0.83 (s, 3H, 19-CH$_3$), 2.09 (s, 3H, 17-OAc), 2.24 (s, 3H, NCH$_3$), 3.08 (m, 1H, 16α-H), 3.67 (m, 1H, hydroxypiperidine-4-H), 3.79 (m, 1H, 3β-H), 4.76 (d, 1H, 17α-H).

EXAMPLE 35

Preparation of 4-[17β-acetyloxy-3α-hydroxy-
2β-(4-hydroxy-1-piperidinyl)-5α-androstan-16β-yl]-
1,1-dimethylpiperazinium bromide 2β-(4-Hydroxy-1-piperidinyl)-16β-(4-methyl-1-piperazinyl)-5α-androstane-3α,17β-diol-17-acetate is reacted with methyl bromide as described in Example 30 to obtain the title compound in a yield of 86.3%, m.p.: 295°–300° C.

$^1$H-NMR:300 MHz (CDCl$_3$) δ ppm: 0.76 (s, 3H, 18-CH$_3$), 0.95 (s, 3H, 19-CH$_3$), 2.09 (s, 3H, 17-OAc), 3.14 (s, 3H, N$^+$CH$_3$), 3.19 (m, 1H, 16α-H), 3.94 (m, 1H, 3β-H), 4.73 (d, 1H, 17α-H).

EXAMPLE 36

Preparation of
4-[17β-acetyloxy-3α-hydroxy-2β-(4-hydroxy-
1-piperidinyl)-5α-androstan-16β-yl]-1-methyl-
1-(2-propenyl)piperazinium bromide (4-Hydroxy-1-piperidinyl)-16β-(4-methyl-1-piperazinyl)-5α-androstane-3α,17β-diol-17-acetate is reacted with allyl bromide as described in Example 31 to obtain the title compound in a yield of 74.2%, m.p.: 274°–277° C.

EXAMPLE 37

Preparation of
16β-(4-methyl-1-piperazinyl)-2β-(4-oxo-
1-piperidinyl)-5α-androstane-3α,17β-diol-diacetate
16β-(4-Methyl-1-piperazinyl)-2β-(4-oxo-
1-piperidinyl)-5α-androstane-3α,17β-diol is
acetylated according to the procedure described in
Example 6 to give the title product as a foam in a
yield of 68.3%.

$^1$H-NMR:300 MHz (CDCl$_3$) δ ppm: 0.81 (s, 3H, 18-CH$_3$), 1.06 (s, 3H, 19-CH$_3$), 2.08 and 2.12 (s, 3H, 3-OAc and 17-OAc), 2.26 (s, 3H, NCH$_3$), 4.80 (d, 1H, 17α-H), 5.29 (m, 1H, 3β-H).

EXAMPLE 38

Preparation of
4-[3α,17β-bis(acetyloxy)-2β-(4-oxo-1-piperidinyl)-
5α-androstan-16β-yl]-1,1-dimethylpiperazinium
bromide 16β-(4-Methyl-1-piperazinyl)-2β-(4-oxo-1-piperidinyl)-5α-androstane-3α,17β-diol-diacetate is reacted with methyl bromide as described in Example 30 to produce the title compound in a yield of 90.5%, m.p.: 215°–220° C. (with decomposition).

$^1$H-NMR:300 MHz (CDCl$_3$) δ ppm: 0.79 (s, 3H, 18-CH$_3$), 1.05 (s, 3H, 19-CH$_3$), 2.09 and 2.13 (s, s, 3H, 3H, 3-OAc and 17-OAc ), 3.56 (s, 6H, N$^+$CH$_3$), 4.82 (d, 1H, 17α-H), 5.28 (m, 1H, 3β-H).

Example 39

Preparation of
4-[3α,17β-bis(acetyloxy)-2β-(4-oxo-1-piperidinyl)-
5α-androstan-16β-yl]-1-methyl-
1-(2-propenyl)piperazinium bromide 16β-(4-Methyl-1-piperazinyl)-2β-(4-oxo-1-piperidinyl)-5α-androstane-3α,17β-diol-diacetate is reacted with allyl bromide as described in Example 31 to give the title compound in a yield of 89.5%, m.p.: 176°–180° C.

EXAMPLE 40

Preparation of
2β-(4-hydroxy-1-piperidinyl)-16β-(4-methyl-
1-piperazinyl)-5α-androstane-3α,17β-diol-diacetate 16β-(4-Methyl-1-piperazinyl)-2β-(4-oxo-1-piperidinyl)-5α-androstane-3α,17β-diol-diacetate is reduced by sodium borohydride as described in Example 11 to obtain the foam-like title compound in a yield of 83.05%, R$_f^2$=0.61.

EXAMPLE 41

Preparation of
4-[3α,17β-bis(acetyloxy)-2β-(4-hydroxy-
1-piperidinyl)-5α-androstan-16β-yl]-
1,1-dimethylpiperazinium bromide 2β-(4-Hydroxy-1-piperidinyl)-16β-(4-methyl-1-piperazinyl)-5α-androstane-3α,17β-diol-diacetate is reacted with methyl bromide as described in Example 30 to obtain the title compound in a yield of 77.7%, m.p.: 250°–253° C.

¹H-NMR:300 MHz (CDCl₃) δ ppm: 0.75 (s, 3H, 18-CH₃), 0.98 (s, 3H, 19-CH₃), 2.00 (s, 3H, 3-OAc), 2.09 (s, 3H, 17-OAc), 3.18 (m, 1H, 16α-H), 3.32 and 3.33 (s, s, 3H, 3H, N⁺CH₃), 3.41 (m, 1H, hydroxypiperidine-4-H), 4.73 (d, 1H, 17α-H), 5.15 (m, 1H, 3β-H).

EXAMPLE 42

Preparation of
4-[3α,17β-bis(acetyloxy)-2β-(4-hydroxy-1-piperidinyl)-5α-androstan-16β-yl]-1-methyl-1-(2-propenyl)piperazinium bromide 2β-(4-Hydroxy-1-piperidinyl)-16β-(4-methyl-1-piperazinyl)-5α-androstane-3α,17β-diol-diacetate is reacted with allyl bromide as described in Example 31 to yield 78% of the title compound.

¹H-NMR:300 MHz (CDCl₃) δ ppm: 0.77 (s, 3H, 18-CH₃), 1.03 (s, 3H, 19-CH₃), 2.07 and 2.12 (s, s, 3H, 3H, 3-OAc and 17-OAc ), 3.44 (s, 3H, N⁺CH₃), 4.57 (m, 2H, N⁺CH₂—CH=), 4.80 (d, 1H, 17α-H), 5.28 (m, 1H, 3β-H), 5.65–6.2 (m, 3H, —CH=CH₂).

EXAMPLE 43

Preparation of
2β-(4-hydroxy-1-piperidinyl)-16β-(4-methyl-1-piperazinyl)-5α-androstane-3α,17β-diol 2α,3α-Epoxy-16β-(4-methyl-1-piperazinyl)-5α-androstane-17β-ol is reacted with 4-hydroxypiperidine as described in Example 3 to obtain the title compound in a yield of 78.57%, m.p.: 248°–250° C.

EXAMPLE 44

Preparation of
2β-(4-acetyloxy-1-piperidinyl)-16β-(4-methyl-1-piperazinyl)-5α-androstane-3α,17β-diol-diacetate 2β-(4-Hydroxy-1-piperidinyl)-16β-(4-methyl-1-piperazinyl)-5α-androstane-3α,17β-diol is acetylated according to the procedure as described in Example 18 to give the title compound in a yield of 68%, $R_f^2$=0.74.

EXAMPLE 45

Preparation of
4-[3α,17β-bis(acetyloxy)-2β-(4-acetyloxy-1-piperidinyl)-5α-androstan-16β-yl]-1,1-dimethylpiperazinium bromide 2β-(4-Acetyloxy-1-piperidinyl)-16β-(4-methyl-1-piperazinyl)-5α-androstane-3α,17β-diol-diacetate is reacted with methyl bromide as described in Example 30 to obtain the title compound in a yield of 87%, $R_f^2$=0.14.

EXAMPLE 46

Preparation of
4-[3α,17β-bis(acetyloxy)-2β-(4-acetyloxy-1-piperidinyl)-5α-androstan-16β-yl]-1-methyl-1-(2-propenyl)piperazinium bromide 2β-(4-Acetyloxy-1-piperidinyl)-16β-(4-methyl-1-piperazinyl)-5α-androstane-3α,17β-diol-diacetate is reacted with allyl bromide as described in Example 31 to obtain the title compound in a yield of 81%, $R_f^2$=0.71.

¹H-NMR:300 MHz (CDCl₃) δ ppm: 0.77 (s, 3H, 18-CH₃), 1.01 (s, 3H, 19-CH₃), 2.03 (s, 3H, 4'-OAc), 2.06 (s, 3H, 3-OAc), 2.12 (s, 3H, 17-OAc), 2.7–3.05 (m, 6H, NCH₂), 3.23 (m, 1H, 16α-H), 3.41 (s, 3H, N⁺CH₃), 3.4–3.87 (m, 4H, N⁺CH₂), 4.54 (m, 2H, N⁺CH₂—CH=), 4.75 (m, 1H, 4'-H), 4.77 (d, 1H, 17α-H), 5.23 (m, 1H, 3β-H), 5.76 and 5.90 (2×dd, 2H, =CH₂), 6.02 (m, 1H, —CH=).

EXAMPLE 47

Preparation of
16β-(1,4-dioxa-8-azaspiro[4.5]dec-8-yl)-2α,3α-epoxy-5α-androstan-17-one 17-Bromo-2α,3α:16α,17α-diepoxy-5α-androstane is reacted with 1,4-dioxa-8-azaspiro[4.5]decane as described in Example 1 to obtain the title compound in a yield of 99.5%, m.p.: 140°–141° C.

EXAMPLE 48

Preparation of
16β-(1,4-dioxa-8-azaspiro[4.5]dec-8-yl)-2α,3α-epoxy-5α-androstane-17β-ol 16β-(1,4-Dioxa-8-azaspiro[4.5]dec-8-yl)-2α,3α-epoxy-5α-androstan-17-one is reduced by using sodium borohydride as described in Example 2 to give the title compound in a yield of 91.1%, m.p.: 186°–188° C.

EXAMPLE 49

Preparation of
16β-(1,4-dioxa-8-azaspiro[4.5]dec-8-yl)-2β-(1-piperidinyl)-5α-androstane-3α,17β-diol 16β-(1,4-Dioxa-8-azaspiro[4.5]dec-8-yl)-2α,3α-epoxy-5α-androstane-17β-ol is reacted with piperidine as described in Example 3 to give the title compound in a yield of 87.5%, m.p.: 183°–185° C.

EXAMPLE 50

Preparation of
16β-(1,4-dioxa-8-azaspiro[4.5]dec-8-yl)-2β-(1-piperidinyl)-5α-androstane-3α,17β-diol-17-acetate 16β-(1,4-Dioxa-8-azaspiro[4.5]dec-8-yl)-2β-(1-piperidinyl)-5α-androstane-3α,17β-diol is acetylated as described in Example 6 to obtain the title compound in a yield of 63.7%, m.p.: 124°–128° C.

EXAMPLE 51

Preparation of
8-[3α,17β-bis(acetyloxy)-2β-(1-piperidinyl)-5α-androstan-16β-yl]-8-methyl-1,4-dioxa-8-azoniaspiro[4.5]decane bromide 16β-(1,4-Dioxa-8-azaspiro[4.5]dec-8-yl)-2β-(1-piperidinyl)-5α-androstane-3α,17β-diol-17-acetate is reacted with methyl bromide as described in Example 7 to give the title compound in a yield of 64.8%, $R_f^2$=0.71.

EXAMPLE 52

Preparation of
2β,16β-bis(1,4-dioxa-8-azaspiro[4.5]dec-8-yl)-
5α-androstane-3α,17β-diol 16β-(1,4-Dioxa-8-azaspiro[4.5]dec-8-yl)-2α,3α-epoxy-17β-hydroxy-5α-androstane is reacted with 1,4-dioxa-8-azaspiro[4.5]decane as described in Example 3 to obtain the title compound in a yield of 80.1%, m.p.: 180°–182° C.

EXAMPLE 53

Preparation of
16β-(1,4-dioxa-8-azaspiro[4.5]dec-8-yl)-
2β-(4-hydroxy-1-piperidinyl)-
5α-androstane-3α,17β-diol 16β-(1,4-Dioxa-8-azaspiro[4.5]dec-8-yl)-2α,3α-epoxy-17β-hydroxy-5α-androstane is reacted with 4-hydroxypiperidine as described in Example 3 to obtain the title compound in a yield of 78.3%, m.p.: 199°–201° C.

EXAMPLE 54

Preparation of 2β-(4-acetyloxy-1-piperidinyl)-16β-(1,4-dioxa-8-azaspiro[4.5]dec-8-yl)-
5α-androstane-3α,17β-diol-diacetate.

16β-(1,4-Dioxa-8-azaspiro[4.5]dec-8-yl)-2β-(4-hydroxy-1-piperidinyl)-5α-androstane-3α,17β-diol is acetylated as described in Example 18 to give the title compound in a yield of 80.8% as a foam-like substance, $R_f^3$=0.59.

EXAMPLE 55

Preparation of
8-[3α,17β-bis(acetyloxy)-2β-(4-acetyloxy-1-piperidinyl)-5α-androstan-16β-yl]-8-methyl-
1,4-dioxa-8-azoniaspiro[4.5]decane bromide 2β-(4-Acetyloxy-1-piperidinyl)-16β-(1,4-dioxa-8-azaspiro[4.5]dec-8-yl)-5α-androstane-3α,17β-diol-diacetate is reacted with methyl bromide as described in Example 7 to obtain the title compound in a yield of 81%, m.p.: 157°–160° C.

EXAMPLE 56

Preparation of
2α,3α-epoxy-16β-(4-hydroxy-1-piperidinyl)-
5α-androstane-17-one

17-Bromo-2α,3α:16α,17α-diepoxy-5α-androstane is reacted with 4-hydroxypiperidine as described in Example 1 to give the title compound in a yield of 95.8%, m.p.: 140°–142° C.

EXAMPLE 57

Preparation of
2α,3α-epoxy-16β-(4-hydroxy-1-piperidinyl)-
5α-androstane-17β-ol

2α,3α-Epoxy-16β-(4-hydroxy-1-piperidinyl)-5α-androstane-17-one is reduced by using sodium borohydride as described in Example 2 to give the title product in a yield of 86.06%, m.p.: 204°–206° C.

EXAMPLE 58

Preparation of
2β-(1,4-dioxa-8-azaspiro[4.5]dec-8-yl)-
16β-(4-hydroxy-1-piperidinyl)-
5α-androstane-3α,17β-diol 2α,3α-Epoxy-16β-(4-hydroxy-1-piperidinyl)-5α-androstane-17β-ol is reacted with 1,4-dioxa-8-azaspiro[4.5]decane as described in Example 3 to obtain the title compound in a yield of 85.90%, m.p.: 253°–255° C.

EXAMPLE 59

Preparation of 2β,16β-bis(4-hydroxy-1-piperidinyl)-
5α-androstane-3α,17β-diol

2α,3α-Epoxy-16β-(4-hydroxy-1-piperidinyl)-5α-androstane-17β-ol is reacted with 4-hydroxypiperidine as described in Example 3 to obtain the title compound in a yield of 85.4%, m.p.: 248°–250° C.

EXAMPLE 60

Preparation of
2β,16β-bis(4-acetyloxy-1-piperidinyl)-
5α-androstane-3α,17β-diol-diacetate After adding 21 ml of triethylamine and then 17 ml of acetyl chloride to 15.0 g of 2β,16β-bis(4-hydroxy-1-piperidinyl)-5α-androstane-3α,17β-diol dissolved in 85 ml of methylene chloride, the solution is left to stand for 12 hours, then the excess of acetyl chloride is decomposed by water. The methylene chloride solution is washed first with an aqueous sodium hydroxide solution cooled to 2°–5° C. and then with water until it becomes neutral. After drying, methylene chloride is evaporated to obtain the title compound as a foam-like residue in a yield of 74.9%, $R_f^3$=0.67.

EXAMPLE 61

Preparation of
4-acetyloxy-1-[3α,17β-bis(acetyloxy)-
2β-(4-acetyloxy-1-piperidinyl)-5α-androstan-
16β-yl]-1-methylpiperidinium bromide 2β,16β-Bis(4-acetyloxy-1-piperidinyl)-5α-androstane-3α,17β-diol-diacetate is reacted with methyl bromide as described in Example 7 to obtain the title compound in a yield of 75%, m.p.: 200°–205° C.

EXAMPLE 62

Lyophilized powder ampoule composition

Mannitol solution of 60 g/liter concentration is prepared by employing twice distilled water for injection use and the solution obtained is filtered to sterile. Simultaneously, a solution of 20 g/liter concentration is prepared from active agent by employing twice distilled water for injection use. This latter solution is also filtered to sterile. Both solutions are combined under aseptic conditions and filled in 1 ml volumes each into ampoules. The content of the ampoules is lyophilized and after filling with nitrogen, the ampoules are sealed to obtain ampoules containing 10 mg of active agent each. Before use, the content of the ampoule is dissolved in physiological saline solution (containing 0.9% of sodium chloride).

EXAMPLE 63

Preparation of 2β-(1,4-dioxa-8-azaspiro[4.5]dec-8-yl)-16β-(1-pyrrolidinyl)-5α-androstane-3α,17β-diol-3-acetate 1.5 g of 2β-(1,4-dioxa-8-azaspiro[4.5]dec-8-yl)-16β-(1-pyrrolidinyl)-5α-androstane-3α,17β-diol-diacetate was dissolved in 10 ml of methanol, thereafter the reaction mixture was warmed to the boiling and maintained at the same temperature for 30 minutes. After completion of the reaction it was cooled to 10° C., the precipitate was filtered off, dried (1.2 g) and recrystallized from acetonitrile to yield 1.0 g, m.p.: 214°–217° C.

EXAMPLE 64

Preparation of 1-[3α-Acetyloxy-2β-(1,4-dioxa-8-azaspiro[4.5]dec-8-yl)-17β-hydroxy-5α-androstan-16β-yl]-1-(2-propenyl)pyrrolidinium bromide 2β-(1,4-Dioxa-8-azaspiro[4.5]dec-8-yl)-16β-(1-pyrrolidinyl)-5α-androstane-3α,17β-diol-3-acetate is reacted with allyl bromide as described in Example 5 to obtain the title compound in a yield of 71%, m.p.: 220°–223° C.

$^1$H-NMR: 300 MHz (CDCl$_3$) δ ppm: 0.86 (s, 3H, 18-CH$_3$), 1.01 (s, 3H, 19-CH$_3$), 2.07 (s, 3H, 3-OAc), 2.43 (br, 1H, 2α-H), 2.62 (br, 4H, NCH$_2$), 3.5–4.1 (m, 6H, N$^+$CH$_2$), 3.94 (s, 4H, CH$_2$O), 4.50 (m, 1H, 16α-H), 5.23 (m, 1H, 3β-H), 5.69 and 5.85 (m, 2H, =CH$_2$), 6.06 (m, 1H, —CH=).

EXAMPLE 65

Preparation of 1-[3α,17β-Dihydroxy-2β-(1,4-dioxa-8-azaspiro[4.5]dec-8-yl)-5α-androstane-16β-yl]-1-(2-propenyl)pyrrolidinium bromide 2β-(1,4-Dioxa-8-azaspiro[4.5]dec-8-yl)-16β-(1-pyrrolidinyl)-5α-androstane-3α,17β-diol is reacted with allyl bromide as described in Example 5 to obtain the title compound in a yield of 82%, m.p.: 238°–240° C.

$^1$H-NMR: 300 MHz (CDCl$_3$) δ ppm: 0.84 and 0.87 (s,s, 3H,3H, 18-CH$_3$ and 19-CH$_3$), 2.45–2.85 (m, 5H, 2α-H and NCH$_2$), 3.5–4.15 (m, 8H, N$^+$CH$_2$, 3β-H and 3-OH), 3.96 (s, 4H, CH$_2$O), 4.29 (m, 1H, 17α-H), 4.53 (m, 1H, 16α-H), 5.77 (d, 1H, 17-OH), 5.70 and 5.89 (m, 2H, =CH$_2$), 6.06 (m, 1H, —CH=).

What we claim is:

1. A compound, selected from the group consisting of:

1-[17β-acetyloxy-2β-(1,4-dioxa-8-azaspiro[4.5]dec-8-yl)-3α-hydroxy-5α-androstan-16β-yl]-1-(2-propenyl)pyrrolidinium bromide;

1-[3α,17β-bis(acetyloxy)-2β-(1,4-dioxa-8-azaspiro[4.5]dec-8-yl)-5α-androstan-16β-yl]-1-methylpyrrolidinium bromide;

1-[3α,17β-bis(acetyloxy)-2β-(1,4-dioxa-8-azaspiro[4.5]dec-8-yl)-5α-androstan-16β-yl]-1-(2-propenyl)pyrrolidinium bromide;

1-[17β-acetyloxy-3α-hydroxy-2β-(4-hydroxy-1-piperidinyl)-5α-androstan-16β-yl]-1-methylpyrrolidinium bromide;

1-[17β-acetyloxy-3α-hydroxy-2β-(4-hydroxy-1-piperidinyl)-5α-androstan-16β-yl]-1-(2-propenyl)pyrrolidinium bromide;

1-[3α,17β-bis(acetyloxy)-2β-(4-hydroxy-1-piperidinyl)-5α-androstan-16β-yl]-1-(2-propenyl)pyrrolidinium bromide;

1-[3α,17β-bis(acetyloxy)-2β-(4-acetyloxy-1-piperidinyl)-5α-androstan-16β-yl]-1-methylpyrrolidinium bromide;

1-[17β-(acetyloxy)-3α-hydroxy-2β-(4-hydroxy-1-piperidinyl)-5α-androstan-16β-yl]-1-methylpiperidinium bromide;

1-[3α,17β-bis(acetyloxy)-2β-(4-hydroxy-1-piperidinyl)-5α-androstan-16β-yl]-1-methylpiperidinium bromide;

4-[3α,17β-bis(acetyloxy)-2β-(1,4-dioxa-8-azaspiro[4.5]dec-8-yl)-5α-androstan-16β-yl]-1,1-dimethylpiperazinium bromide;

4-[3α,17β-bis(acetyloxy)-2β-(1,4-dioxa-8-azaspiro[4.5]dec-8-yl)-5α-androstan-16β-yl]-1-methyl-1-(2-propenyl)piperazinium bromide;

4-[17β-acetyloxy-3α-hydroxy-2β-(4-hydroxy-1-piperidinyl)-5α-androstan-16β-yl]-1,1-dimethylpiperazinium bromide;

4-[17β-acetyloxy-3α-hydroxy-2β-(4-hydroxy-1-piperidinyl)-5α-androstan-16β-yl]-1-methyl-1-(2-propenyl)piperazinium bromide;

4-[3α,17β-bis(acetyloxy)-2β-(4-oxo-1-piperidinyl)-5α-androstan-16β-yl]-1,1-dimethylpiperazinium bromide;

4-[3α,17β-bis(acetyloxy)-2β-(4-oxo-1-piperidinyl)-5α-androstan-16β-yl]-1-methyl-1-(2-propenyl)piperazinium bromide;

4-[3α,17β-bis(acetyloxy)-2β-(4-hydroxy-1-piperidinyl)-5α-androstan-16β-yl]-1,1-dimethylpiperazinium bromide;

4-[3α,17β-bis(acetyloxy)-2β-(4-hydroxy-1-piperidinyl)-5α-androstan-16β-yl]-1-methyl-(2-propenyl)piperazinium bromide;

4-[3α,17β-bis(acetyloxy)-2β-(4-acetyloxy-1-piperidinyl)-5α-androstan-16β-yl]-1,1-dimethylpiperazinium bromide;

4-[3α,17β-bis(acetyloxy)-2β-(4-acetyloxy-1-piperidinyl)-5α-androstan-16β-yl]-1-methyl-1-(2-propenyl)piperazinium bromide;

8-[3α,17β-bis(acetyloxy)-2β-(1-piperidinyl)-5α-androstan-16β-yl]-8-methyl-1,4-dioxa-8-azoniaspiro[4.5]decane bromide;

8-[3α,17β-bis(acetyloxy)-2β-(4-acetyloxy-1-piperidinyl)-5α-androstan-16β-yl]-8-methyl-1,4-dioxa-8-azoniaspiro[4.5]-decane bromide;

4-acetyloxy-1-[3α,17β-bis(acetyloxy)-2β-(4-acetyloxy-1-piperidinyl)-5α-androstan-16β-yl]-1-methylpiperidinium bromide;

1-[3α-acetyloxy-2β-(1,4-dioxa-8-azaspiro[4.5]dec-8-yl)-17β-hydroxy-5α-androstan-16β-yl]-1-(2-propenyl)pyrrolidinium bromide; and 1-[3α,17β-dihydroxy-2β-(1,4-dioxa-8-azaspiro[4.5]dec-8-yl)-5α-androstan-16β-yl]-1-(2-propenyl)pyrrolidinium bromide.

2. A pharmaceutical composition with neuromuscular blocking effect, which comprises as an active ingredient a therapeutically effective amount of one or more androstane derivative(s) of claim 3 or a pharmaceutically acceptable acid addition salt thereof, in admixture with filling, diluting, stabilizing, pH- and osmotic pressure-adjusting and/or formulation-promoting additives commonly used in the pharmaceutical industry.

3. Method for blocking the transmission of nerve impulses to striated muscles, characterized by administering to a mammal to be treated a therapeutically effective amount of one or more androstane derivative(s) of claim 3 or a pharmaceutically acceptable acid addition salt thereof alone or in the form of a pharmaceutical composition.

4. A compound as claimed in claim 3, which is 1-[3α,17β-bis(acetyloxy)-2β-(1,4-dioxa-8-azaspiro[4.5]-dec-8-yl)-5α-androstan-16β-yl]-1-(2-propenyl)pyrrolidinium bromide or a pharmaceutically acceptable acid addition salt thereof.

5. A compound as claimed in claim 3, which is 1-[17β-acetyloxy-2β-(1,4-dioxa-8-azaspiro[4.5]-dec-8-yl)-3α-hydroxy-5α-androstan-16β-yl]-1-(2-propenyl)pyrrolidinium bromide or a pharmaceutically acceptable acid addition salt thereof.

6. A method as claimed in claim 3, wherein the androstane derivative is 1-[3α,17β-bis(acetyloxy)-2β-(1,4-dioxa-8-azaspiro[4.5]-dec-8-yl)-5α-androstan-16β-yl]-1-(2-propenyl)pyrrolidinium bromide.

7. A compound as claimed in claim 3, which is 4-[3α,17β-bis(acetyloxy)-2β-(4-hydroxy-1-piperidinyl)-5α-androstan-16β-yl]-1,1-dimethylpiperazinium bromide or a pharmaceutically acceptable acid addition salt thereof.

8. A method as claimed in claim 3, wherein the androstane derivative is 4-[3α,17β-bis(acetyloxy)-2β-(4-hydroxy-1-piperidinyl)-5α-androstan-16β-yl]-1,1-dimethylpiperazinium bromide.

* * * * *

UNITED STATES PATENT AND TRADEMARK OFFICE
CERTIFICATE OF CORRECTION

PATENT NO. : 5,591,735
DATED : January 7, 1997
INVENTOR(S) : Zoltan TUBA et al.

It is certified that error appears in the above-identified patent and that said Letters Patent is hereby corrected as shown below:

On the cover sheet, left column, section [73], change "Marvishi" to --Maruishi--.

Signed and Sealed this

Nineteenth Day of August, 1997

Attest:

BRUCE LEHMAN

Attesting Officer
Commissioner of Patents and Trademarks